United States Patent [19]

Roth et al.

[11] 4,223,129

[45] Sep. 16, 1980

[54] CONTINUOUS PROCESS FOR MAKING ALKYL ALDOSIDES FROM STARCH OR OTHER CARBOHYDRATES

[75] Inventors: Claris D. Roth; Kenneth B. Moser; William A. Bomball, all of Decatur, Ill.

[73] Assignee: A. E. Staley Manufacturing Company, Decatur, Ill.

[21] Appl. No.: 938,750

[22] Filed: Sep. 1, 1978

[51] Int. Cl.$^2$ .............................................. C07H 1/00
[52] U.S. Cl. .......................................... 536/4; 536/120
[58] Field of Search ...................................... 536/4, 120

[56] References Cited

U.S. PATENT DOCUMENTS

| | | | |
|---|---|---|---|
| 2,276,621 | 3/1942 | Langlois | 536/4 |
| 2,390,507 | 12/1945 | Cantor | 536/4 |
| 3,165,508 | 1/1965 | Otey et al. | 536/4 |
| 3,296,245 | 1/1967 | Kaiser et al. | 536/4 |
| 3,346,558 | 10/1967 | Roth | 536/4 |
| 3,375,243 | 3/1968 | Nevin et al. | 536/4 |
| 3,450,690 | 6/1969 | Gibbons et al. | 536/4 |
| 3,531,461 | 9/1970 | Hamilton et al. | 536/4 |
| 3,565,885 | 2/1971 | Molotsky et al. | 536/4 |
| 3,598,865 | 8/1971 | Lew | 536/4 |
| 3,707,535 | 12/1972 | Lew | 536/4 |

*Primary Examiner*—Johnnie R. Brown
*Attorney, Agent, or Firm*—M. Paul Hendrickson; Charles J. Meyerson

[57] ABSTRACT

A continuous process for making alkyl aldosides from polysaccharides and more particularly mixed alkyl glycosides from starch by direct alcoholysis. A polysaccharide, such as starch, is slurried in an alcohol and passed through a heated, confined zone under pressure in the presence of an acid catalyst to form a mixed alkyl aldoside. The alcohols which may be used include methanol, ethanol, propanol and butanol, their isomers and mixtures thereof. Higher alkyl glycosides are surfactants and, in some instances, it is advantageous to use higher alcohols, such as decyl and dodecyl alcohols, to obtain particular surfactant properties in the resulting alkyl glycosides. Mixed alkyl glycosides are useful in detergent applications, and as backbone polymers in polyurethane foams.

15 Claims, No Drawings

CONTINUOUS PROCESS FOR MAKING ALKYL ALDOSIDES FROM STARCH OR OTHER CARBOHYDRATES

BACKGROUND

Alkyl aldosides are important industrial products which can be used as intermediates in the synthesis of surfactants and to make polyol glycosides which are useful as initiators in the manufacture of rigid polyurethane foams. There is considerable prior art regarding various methods of making alkyl glycosides. However, to applicants' knowledge, there has not been a successful continuous method of making alkyl glycosides directly from starch.

There are some important economic advantages in a continuous process for making alkyl glycosides from starch. For example, starch is a plentiful and inexpensive raw material. It can be easily handled and can be readily slurried in a lower alcohol such as methanol.

In a continuous reaction process, there is less waste of reagents. Higher temperatures, but for much less time, can be used to drive the reaction to completion. Higher yields of purer product can be obtained because the heating is instantaneous and under pressure. There is less opportunity for the formation of color bodies, and for side reactions which form undesirable impurities. In addition, repolymerization of the alkyl glycosides obtained from the continuous alcoholysis process is minimized because the temperature of the reaction mixture drops almost instantaneously after leaving the reaction zone.

PRIOR ART

Expired U.S. Pat. No. 2,276,621 is directed to a batch method of making a high yield alpha-methyl glucoside. The reaction is carried out in the presence of a strong mineral acid catalyst, preferably sulfuric acid. Starch is used as the starting material, but other carbohydrates may also be used. The reaction is performed in the presence of an excess of methanol in order to increase the proportionate amount of alpha-methyl glucoside produced. After the reaction, which takes about two hours at 100° C., the reaction mixture is transferred to an evaporator where methanol is removed to bring the resulting liquor to a concentration of 35-40% solids. The concentrated mixture is then allowed to crystallize.

G. R. Dean et al. disclosed the use of a cation exchange material catalyst in U.S. Pat. No. 2,606,186. The cation exchange material replaces the more typical mineral acid catalyst in a reaction of dextrose with methanol to form methyl alpha-D-glucoside and methyl beta-D-glucoside. The reaction time disclosed is from 1-48 hours and the temperature is limited to about 100° C. in order to avoid damaging the resin. Typical resins employed are sulfonated-type cation exchangers including sulfonated phenol-formaldehyde cation exchange resins, sulfonated polystyrene cation exchange resins, and sulfonated coal-type cation exchange resins.

The above Dean et al. patent describes a continuous process for making methyl glucoside from anhydrous dextrose and methanol in the presence of the described resin catalyst. Initially, anhydrous dextrose is added to methanol to make a 30% dry substance slurry. This slurry is then mixed with the resin catalyst so that the catalyst is present in an amount equivalent to 25% of the total dry substance. This mixture is heated and agitated, and as methyl glucoside is produced, it goes into solution. This solution is then pumped through a column containing additional resin. The column is provided with an external jacket containing steam to maintain the jacket at a temperature of about 110° C. After the reaction, methanol is removed by flashing, the evacuated liquor is then concentrated and crystallized. Crystalline methyl glucoside is then separated centrifugally.

U.S. Pat. No. 2,735,792 describes a continuous coil reactor for acid converting starch under elevated temperature and pressure. In the example given, a 24° Be acidified starch slurry is pumped through the continuous coil reactor at a temperature of at least 160° C. and a pressure of 15 kg/cm$^2$. This system avoids any direct contact between the steam used to heat the coil reactor and the starch. The patent states that all particles of the starch medium are subjected to uniform treatment, thereby avoiding excessive hydrolysis of some of the starch particles. In addition, this patent points out that the uninterrupted movement through the coil-type reactor eliminates possible clogging.

U.S. Pat. No. 3,296,245 is directed to a batch process for making methyl alpha-D-glucoside directly from starch using a Lewis acid catalyst under pressure. A mixture of methanol, starch and BF$_3$ etherate is heated to 135° C. under N$_2$ pressure of 200-350 p.s.i. The heating time is 90 minutes, and after the resulting liquor product mixture is neutralized, and the methanol content reduced, crystalline methyl glucoside is separated by filtration at a yield of about 41%. It is believed that this method would add considerable expense to the product.

Roth describes a continuous process for making polyol glycosides in U.S. Pat. No. 3,346,558. A mixture comprising starch, polyol and acid is subjected to intense mechanical working at a temperature of at least 170° C. under pressure. The starch is converted into polyol glycosides without passing through an unworkable gel state. A screw-type plastics extruder can be used to provide the necessary working or shearing of the starch composition. The method described utilizes various catalysts including sulfonic acids, Lewis acids, and strong mineral acids. The particular polyols employed in this process include ethylene glycol, sorbitol and glycerol, and the resulting products are longer chain glycols.

"Methanolysis of Starch" is described in the following reference: Whistler et al., *Methods In Carbohydrate Chemistry*, Volume 4, pages 272-275. The process described is non-continuous, and the reaction time is about two hours.

More recently, U.S. Pat. No. 3,375,243 issued to Nevin et al. This patent describes a method of making methyl glucosides from starch using p-toluene sulfonic acid catalyst in a pressure reactor at 165° C. and at about 275 p.s.i.g. pressure. It is reported there that approximately 85-90% of the starch was converted to methyl glucoside. The specification describes reaction temperatures in the range of 100°-250° C.

U.S. Pat. No. 3,450,690, describes the preparation of alkali-stable alkyl glucosides by alkaline treatment to remove impurities. Crude alkyl glucosides in an aqueous solution are subjected to a temperature in the range of 50°-200° C. at a pH of at least 8 for a sufficient period of time to permit conversion of the impurities in the crude solution to a readily separable form. These impurities are then removed.

Molotsky et al., U.S. Pat. No. 3,565,885, describe the preparation of color stable glycosides by means of ion exchange. This patent appears to be a further improvement of U.S. Pat. No. 3,450,690. A portion of the unreacted alcohol in the crude glycoside-alcohol mixture is replaced with water, and the crude glycoside mixture is then contacted with an ion exchange resin to yield a color stable glycoside.

U.S. Pat. No. 3,617,383 describes a continuous process for physically modifying starch which is slurried in a lower alcohol, such as methanol, ethanol and the like. This patent, and a group of related patents, utilize a continuous reactor to momentarily subject a starch/alcohol slurry to high temperatures in a confined zone. In this patent, loss of birefringence without loss of granule structure is described to obtain a cold-water-swelling starch. Although this patent and the related patents disclose treating starches which have previously been chemically modified, these references do not disclose continuous chemical modification of starch in a suitable reactor. In this reference, the temperature and pressure are intentionally controlled to avoid pregelatinizing the starch and to avoid causing the starch to react with the alcohol solvent.

Panusch et al., in U.S. Pat. No. 3,928,318, describe a process for making methyl glucoside in which anhydrous calcium sulfate is used to remove water from the reaction mixture so that higher yields are obtainable. A stainless steel reactor is employed in this batch process.

SUMMARY

This invention is directed to a continuous alcoholysis process for making mixed aldoside from polysaccharides and, more particularly, for making mixed alkyl glycosides directly from starch. The starch is slurried in alcohol and passed through a confined zone under pressure at an elevated temperature in the presence of an acid catalyst to produce a mixture of glycosides, including alpha-alkyl glucoside and beta-alkyl glucoside. The confined zone may comprise a continuous coil reactor having heating means to obtain a reaction temperature in the range of 100°–400° C. for a relatively brief reaction time ranging from about 2–150 minutes. The concentration of catalyst is about 0.001 to 0.1 mole per mole of polysaccharide, and may be any one or more of the following: hydrochloric acid, sulfuric acid, phosphoric acid, ortho-, meta-, and para-toluene-sulfonic acid, benzene-sulfonic acid, various substituted benzene-sulfonic acids, such as ortho-, meta-, and para-bromobenzenesulfonic acids, ethane-sulfonic acid, and others, as well as combinations of the above. About 0.005 mole of catalyst per mole of starch is the presently preferred amount of catalyst for the reaction.

Under ideal conditions of temperature and pressure, and when proper amounts of catalyst are employed, a relatively greater proportion of alpha- and beta-methyl glucosides are formed. Typical amounts in the crude product are: about 49% alpha-methyl glucoside; 24% beta-methyl glucoside; 6% methyl furanosides; 14% methyl maltosides; 3% methyl maltotriosides; about 3.5% reducing sugars; and less than about 0.5% higher molecular weight compounds.

The crude mixed alkyl glycosides may be isolated from the reaction mixture by first adjusting the pH to about 8–10, and then evaporating away most of the methanol. The resulting glycoside mixture is then melted at a temperature high enough to drive off the residual methanol and water. The glycoside mixture is then rapidly cooled to produce a "glass," which can be broken up if desired.

The subject method is performed in a continuous tube-type reactor, which is less expensive than comparable volume, batch type equipment. The reaction takes less time, and produces a high yield of mixed methyl glycoside product.

DETAILED DESCRIPTION

Apparatus of the type disclosed in U.S. Pat. No. 2,735,792 and 3,617,383 may be used in practicing the method of the invention. The apparatus should include a heated, continuous coil reactor, a pressure feed vessel and means for establishing a positive pressure in the feed vessel to force the starch/alcohol slurry through the heated, continous coil reactor. The continuous coil of the reactor may be any convenient length from about 50 to 5,000 feet, and the inner diameter thereof may range from about 0.18 inch to about 6.0 inches. Control means are included to regulate flow pressure and temperature in the continuous coil reactor, and collecting vessel is provided to collect crude product which has been reacted in the continuous coil reactor. Metering means to automatically measure flow through the reactor and to replenish the reactants in the correct proportions in the feed pressure vessel may be provided. A second feed pressure vessel with appropriate valves may be provided in a parallel line with the first, and the reactants can be alternately fed to the continuous coil reactor from either pressure feed vessel as desired.

One embodiment of the system in a more simple form, is outlined below:

I. FEED PRESSURE VESSEL
   (includes pressure feed means, e.g. pressurized gas or pump)
II. CONTINUOUS COIL REACTOR
   (includes heating means, e.g. steam jacket)
III. COLLECTING VESSEL
   (may include cooling means, e.g. cooling water heat exchanger)

The examples below describe specific conditions to produce particular mixed glycoside compositions.

EXAMPLE 1

Starch containing about 5% moisture was slurried in methanol at 43% solids. About 0.005 mole of p-toluene-sulfonic acid per mole AGU (anhydroglucose unit) was added. The continuous reactor was adjusted to provide a temperature of about 165° C. therein as the starch/acid/alcohol slurry mixture passed through. The pressure control means was adjusted to obtain about ten minutes retention time in the continuous coil reactor.

The resulting crude methyl glycoside product was obtained as a 62% solids solution in methanol. It analyzed as follows:

| | |
|---|---|
| 48.0% | methyl-alpha-D-glucopyranoside |
| 25.0% | methyl-beta-D-glucopyranoside |
| 6.0% | methyl-alpha-D-glucopyranoside and methyl-beta-D-glucopyranoside |
| 13.5% | methyl-alpha-D-maltoside and methyl-beta-D-maltoside. |
| 3.0% | methyl-alpha-D-maltotrioside and methyl-beta-D-maltotrioside. |
| 0.3% | higher oligosides |
| 2.0% | dextrose |
| 1.5% | unidentified component (possibly a 5-carbon reducing sugar) |
| 0.7% | residual catalyst and/or moisture |
| 100.0% | |

EXAMPLE 2

The following results were obtained when the reaction was performed using decreasing methanol/starch molar ratio. The methanol/starch ratio was decreased in seven steps from 15:1 to 6.8:1, while maintaining all other variables constant. All runs were at 172° C., 16 minutes retention time, using 0.01 mole of para-toluenesulfonic acid catalyst per mole of anhydroglucose unit (AGU) based on starch adjusted to 5% moisture. As set forth below, it can be seen that this change reduced the percentage of alpha- and beta-methyl glucosides in the crude product while the levels of dextrose and polyglycosides increased. See Table I below:

EXAMPLE 3

Tests were made to determine the effect of reducing the amount of catalyst used. Para-toluene sulfonic acid was reduced from 0.01 to 0.005 mole/mole AGU (anhydroglucose unit) in a series of tests. There was no observable change in the chemical composition of the product. However, at 0.0034 mole catalyst/mole AGU, the reactor plugged. Product color at the 0.005 mole catalyst level was significantly lighter than at higher levels. The results for four samples having various levels of para-toluene sulfonic acid catalyst are set forth below:

TABLE II
Effect of Catalyst Level of Product Composition

| Sample | H* | I | J | K |
|---|---|---|---|---|
| Moles Catalyst/Mole AGU | 0.010 | 0.0066 | 0.0050 | 0.0034 |
| Product Compositon: | | | | |
| methyl-beta, % | 45.67 | 46.31 | 46.64 | |
| methyl-beta-D-glucopyranoside, % | 25.88 | 25.62 | 25.75 | |
| alpha- and beta-methyl diglycosides, % | 14.17 | 14.40 | 14.31 | Not |
| alpha- and beta-methyl triglycosides, % | 3.10 | 3.18 | 2.93 | Analyzed |
| Higher glycosides, % | 0.18 | 0.16 | 0.12 | |
| alpha- and beta-glucofuranosides, % | 6.78 | 6.96 | 6.87 | |
| Dextrose, % | 2.33 | 1.70 | 1.67 | |
| Other and unidentified, % | 1.88 | 1.66 | 1.70 | |
| Color | Dk. Brown | Brown | Cream | |

*Same as Sample G, TABLE I.
All runs at 6.8:1 moles methanol-mole AGU, 172° C., 15–16 minutes retention time, PFP starch at 5.0% moisture.

TABLE I
Effect of Decreasing Methanol:Starch Ratio of Product Composition

| Sample | A | B | C | D | E | F | G |
|---|---|---|---|---|---|---|---|
| Moles Methanol/Mole AGU | 15.0 | 12.5 | 10.7 | 9.4 | 8.3 | 7.5 | 6.8 |
| Product Composition | | | | | | | |
| methyl-alpha-D-glucopyranoside % | 51.54 | 51.46 | 50.27 | 50.01 | 48.72 | 47.38 | 45.67 |
| methyl-beta-D-glucopyranoside, % | 27.96 | 27.74 | 27.82 | 27.71 | 26.37 | 26.17 | 25.88 |
| methyl-alpha-D-maltoside and methyl-beta-D-maltoside, % | 8.67 | 9.45 | 10.54 | 11.24 | 12.53 | 13.37 | 14.17 |
| methyl-alpha-D-maltotrioside and methyl-beta-D-maltotrioside % | 1.04 | 1.01 | 1.36 | 1.62 | 2.26 | 2.51 | 3.10 |
| Higher glycosides, % | 0.08 | 0.05 | 0.06 | 0.09 | 0.10 | 0.13 | 0.18 |
| alpha- and beta-glucofuranosides, % | 7.54 | 7.28 | 6.93 | 6.66 | 6.57 | 6.73 | 6.78 |
| Dextrose, % | 1.02 | 1.16 | 1.46 | 1.65 | 1.77 | 2.01 | 2.33 |
| Other and unidentified, % | 2.15 | 1.84 | 1.66 | 1.62 | 1.67 | 1.70 | 1.88 |

All runs at 172° C., 16 minutes retention time, 0.01 mole para-toluene sulfonic acid/mole AGU on PFP starch adjusted to 5% moisture In the above Table I, it can be seen tht Sample A product composition gave a yield of 79.0% methyl-alpha-D-glucopyranoside and methyl-beta-D-glucopyranoside, and only 10.81% of polyglycosides and dextrose. Sample D produced 77.12% methyl-alpha-D-glucopyranoside and methyl-beta-D-glucopyranoside, while Sample G produced only 71.55% of the glucosides. At the same time, the percentages of polyglycosides and dextrose increased as the methanol:starch ratio decreased. The cost of removal of excess methanol must be balanced against the slightly increased yield of glucosides.

Sample K was not analyzed because it plugged the reactor. It appears that a different reactor design may be required for lower catalyst levels. The preferred amount of catalyst using the present reactor is about 0.0050 moles catalyst/mole AGU, although 0.004 moles catalyst/mole AGU was used in one comparison in Example 4, below.

EXAMPLE 4

Tests were also done to determine the effect of temperature on the resulting composition. Temperature of the reaction mixture was changed in four steps from 178° C. to 161° C. with the results reported below:

TABLE III

Effect of Reaction Temperature on Product Composition

| Sample | L | M | N | O |
|---|---|---|---|---|
| Product Composition: | | | | |
| alpha-methyl glucoside, % | 45.79 | 45.89 | 47.29 | 46.61 |
| methyl-beta-D-glucopyranoside, % | 25.96 | 25.80 | 26.21 | 25.92 |
| alpha- and beta-methyl diglycosides, % | 13.70 | 14.53 | 13.87 | 14.14 |
| alpha- and beta-methyl triglycosides, % | 2.97 | 3.08 | 2.89 | 3.49 |
| Higher glycosides, % | 0.23 | 0.29 | 0.28 | 1.19 |
| alpha- and beta-glucofuranosides, % | 6.97 | 6.42 | 6.15 | 5.78 |
| Dextrose, % | 2.08 | 1.91 | 1.66 | 1.51 |
| Other and unidentified, % | 2.29 | 2.08 | 1.64 | 1.35 |
| Reactions Temp., °C. | 178 | 172 | 166 | 161 |
| Color | Brown | Dark Tan | Tan | Cream |

All runs at 6.8:1 moles methanol:mole AGU, 0.005 mole p-TSA/mole, AGU, 16 minutes retention time on PFP starch at 5.0% moisture.

In one experiment, the reaction temperature was increased to 181° C. while decreasing the catalyst to 0.004 mole/mole AGU. Product composition showed only minor changes in almost all components when compared to a run at 172° C. where the catalyst level was 0.005 mole/mole AGU. Color was significantly poorer, however.

As can be seen above in Table III, product color improves from brown to cream. The chemical compositions changed very little, with the only significant increase occurring in the higher glycosides at the lowest temperature.

EXAMPLE 5

The combined effect of reducing the reaction temperature to 152° C. while increasing the retention time to 26 minutes was compared to a run at 172° C. and 16 minutes retention time. The results are reported below:

TABLE IV

Effect of Low Temperature and Increase in Retention Time on Composition

| Sample | P* | Q |
|---|---|---|
| Product Composition: | | |
| apha-methyl glucoside, % | 46.31 | 47.65 |
| methyl-beta-D-glucopyranoside | 25.62 | 26.20 |
| alpha- and beta-methyl diglycosides, % | 14.40 | 14.47 |
| alpha- and beta-methyl triglycosides, % | 3.18 | 3.04 |
| Higher glycosides, % | 0.16 | 0.42 |
| alpha- and beta-glucofurnosides, % | 6.96 | 5.01 |
| Dextrose, % | 1.70 | 1.79 |
| Other and unidentified, % | 1.66 | 1.42 |
| Reaction Temp. °C. | 172 | 152 |
| Retention Time, min. | 16 | 26 |

*Same as Sample I, Table II.
Both runs at 6.8:1 moles methanol/mole AGU, 5% moisture on feed starch, 0.0066 mole p-TSA/Mole AGU.

It can be seen in Table IV that the combination of lower reaction temperature and longer retention time did not avoid the trend toward increase in higher oligosides and dextrose observed above in Table III. The results reported in Table IV for Sample Q indicate that a higher temperature is preferred to avoid an increase of higher oligosides and dextrose, even though the amount of alpha-methyl glucosides produced did not decrease in this comparison.

EXAMPLE 6

The effect of feed starch moisture on product quality was also checked by conducting four runs at feed starch moisture levels ranging from 2% to 11%. The results are reported below:

TABLE V

Effect of Feed Starch Moisture on Product Composition

| Sample | R | S | T | U |
|---|---|---|---|---|
| Product Composition: | | | | |
| alpha-methyl glucoside, % | 48.17 | 45.05 | 45.78 | 48.59 |
| methyl-beta-D-glucopyranoside | 26.78 | 28.46 | 27.86 | 26.33 |
| alpha- and beta-methyl diglycosides, % | 12.67 | 13.16 | 12.76 | 11.88 |
| alpha- and beta-methyl triglycosides, % | 2.49 | 2.40 | 2.23 | 2.09 |
| Higher glucosides, % | 0.07 | 0.09 | 0.07 | 0.15 |
| alpha- and beta-glucofuranosides, % | — | 7.32 | 7.00 | 6.48 |
| Dextrose, % | 1.07 | 1.68 | 2.22 | 2.74 |
| Other and unidentified, % | — | 1.84 | 2.09 | 1.73 |
| Feed starch moisture, % | 2.00 | 5.00 | 8.00 | 11.00 |

All runs at 8.3:1 mole methanol:mole AGU, 0.005 moles p-TSA/mole AGU, 14.5 minutes retention time, 172° C.

It can be seen from the above results in Table V that the percentage of dextrose produced increases as moisture increases. Quite surprisingly, the product also becomes unexpectedly lighter. This improvement in color is opposite to the expected trend. It would be expected that higher dextrose levels would cause darker color. Starch is usually available at about 10–13% moisture, and the above results show that it is not necessary to predry the starch prior to use in the subject process.

EXAMPLE 7

Tests were carried out to determine the effect of retention time on product composition. Retention time of 16.5, 10.7 and 8.0 minutes in the reactor were compared with the results reported below:

TABLE VI

| Sample | V | W | X |
|---|---|---|---|
| Product Composition: | | | |
| alpha-methyl glucoside, % | 44.88 | 45.66 | 43.21 |
| methyl-beta-D-glucopyranoside | 27.68 | 27.58 | 27.54 |
| alpha- and beta-methyl diglycosides, % | 14.44 | 14.04 | 14.73 |
| alpha- and beta methyl triglycosides, % | 2.95 | 2.84 | 3.92 |
| Higher glycosides % | 0.25 | 0.25 | 0.85 |
| alpha- and beta-methyl glucofuranosides, % | 5.26 | 4.79 | 6.03 |
| Dextrose, % | 2.95 | 3.34 | 2.12 |
| Other and unidentified, % | 1.60 | 1.52 | 1.59 |
| Retention Time, min., | 16.50 | 10.70 | 8.00 |

All runs at 6.8:1 mole methanol:mole AGU, 0.005 moles, p-TSA/mole AGU, 167° C., PFP starch at 5.0% moisture.

All of the above runs were performed at 167° C. It can be seen from Table VI that increasing the retention time from 8 to 16.5 minutes favors increased alpha-methyl glucoside yields, and a decrease in the levels of polyglycosides.

In general, the subject method is capable of producing alpha- and beta-methyl glucosides in relatively high yields from about 65.0% to 90.0%. The resulting products are substantially more free of unwanted by-products, and it is believed the continuous reaction assures that a product of more uniform, acceptable quality will be obtained, since the reagents are thoroughly mixed, and each part of the starch slurry is subjected to substantially the same conditions of temperature and pressure, and is rapidly cooled after the reacted product leaves the confined zone of the continuous coil reactor.

The key to the success of the subject continuous method in producing more pure, mixed methyl glycosides at higher total yields is in the fact that the alcohol-slurried starch is heated very quickly to obtain the catalyzed alcoholysis reaction to make the desired product. The slurry is then immediately cooled when the desired product has been obtained.

The advantages of the above procedure include the fact that repolymerization of the methyl glucosides to less desirable polyglycosides is avoided. In addition, undesirable side reactions, which lower yields and give more color bodies, are avoided by the subject method. The composition of the resulting mixed methyl glycosides is surprisingly uniform and consistent in properties.

Other polysaccharide materials can be treated by substantially the same method as described herein. For example, hemi-cellulose, inulin, dextran, xylan and the like, may all be "alcoholized" in the presence of a catalyst to form the corresponding aldosides. The temperatures and pressures are adjusted, of course, to obtain the optimum yields. Corn syrup solids can be used under proper conditions of temperature and pressure to make alkyl glycosides.

In summary, the subject method produced a better product of better color. The product is more uniform, and much smaller equipment can be used, with less necessary capital investment. Because the total reaction cycle takes less time, the method is more energy efficient. There is no separate "heat-up", which saves considerable energy. The total reaction time is most typically from about 6–15 minutes, although it can be as long as thirty minutes.

If desired, the product may be isolated by vacuum evaporation and sudden chilling. This may be accomplished by passing the reaction product through a thin film evaporator and thereafter disposing the evaporated product on a chilled, stainless steel belt. A "glass" is produced on the steel belt, which is then pulverized and dried. Chromatographic separation of the pure chemical products is also possible.

When the mixed methyl glycoside product is made in the same location as it is to be used, special isolation steps are unnecessary. The desolventized product can be used directly to make polyether polyols used in making polyurethane foams. Methyl glycosides also are used as intermediates in making biodegradable nonionic surfactants, and in polymeric coatings.

We claim:

1. A method for directly and continuously converting a polysaccharide and monohydric alcohol slurry into a glycoside mixture, said method comprising the steps of:
   (a) continuously providing to a tubular reaction zone under a positive fluid pressure, a fluid feed slurry consisting essentially of polysaccharide, monohydric alcohol in an amount exceeding the polysaccharide weight and an effective amount of an acid catalyst sufficient to catalyze the conversion of said polysaccharide and monohydric alcohol to a glycoside mixture at an elevated temperature within said reaction zone;
   (b) heating said feed slurry within said continuous tubular reaction zone to an elevated temperature for a period of time sufficient to convert said fluid slurry into a fluid glycoside mixture while continuously providing additional feed slurry to said tubular reaction zone under a positive fluid pressure to force the converted fluid glycoside mixture through said tubular reaction zone; and
   (c) rapidly cooling and recovering the converted glycoside mixture from said tubular reaction zone.

2. The method of claim 1, wherein the polysaccharide and monohydric alcohol respectively consist essentially of starch and alkanol containing from 1 to 4 carbon atoms inclusive, and the slurry is heated and maintained under pressure and at an elevated temperature within said reaction zone for a period of time sufficient to convert the slurry to a glycoside mixture containing from about 65 to 90% alpha-alkyl glucoside and beta-alkyl glucoside.

3. The method of claim 1, in which the monohydric alcohol consists essentially of methanol, the continuous tubular reactor has a total length of at least about 50 feet, and has an internal diameter of about 0.18 to 6.0 inches, the temperature of the slurry within the reaction zone is maintained between 100°–400° C., and the average reaction time in the reaction zone ranges from about 2–30 minutes with said reaction conditions being sufficient to provide a glycoside mixture comprised of (in percent by weight):
   45.67–51.54 alpha-methyl glucoside;
   25.88–27.96 beta-methyl glucoside;
   8.67–14.73 alpha- and beta- methyl diglycoside;
   1.04–3.92 alpha- and beta- methyl triglycoside;
   0.07–1.19 higher methyl glycoside;
   5.26–7.54 glucofuran; and
   1.02–3.34 dextrose.

4. The method of claim 1 wherein the monohydric alcohol is at least one member selected from the group consisting of allyl alcohol and an alkanol containing from one to eighteen carbon atoms inclusive.

5. The method of claim 4, in which the catalyst is selected from the group consisting of hydrochloric acid, sulfuric acid, ortho-, meta-, and para-toluene-sulfonic acid, benzene-sulfonic acid, phosphoric acid, substituted benzene-sulfonic acids, ethane-sulfonic acid and combinations of the above.

6. The method of claim 5, in which the polysaccharide is starch, and the catalyst concentration in the slurry is continuously adjusted to the range of about 0.001 to 0.1 mole per mole of starch, dry solids basis.

7. The method of claim 6 wherein the feed slurry contains about 40–50% starch solids and acid catalyst and from about 50 to 60% methanol, with sufficient methanol being evaporated from the methyl glycoside mixture obtained from said reaction zone to provide at least 55% methyl glycoside mixture solids.

8. The method of claim 6, in which the average reaction time at elevated temperature is about 2–150 minutes and the temperature is quickly lowered after the conversion whereby a substantially pure alkyl glycoside mixture having a low color contamination and a minimum of by-products is obtained.

9. A method for direct, continuous alcoholysis of starch to a mixture of alkyl glycosides, said method comprising the steps of: continuously making a fluid slurry of starch in monohydric alcohol in which the amount by weight of monohydric alcohol exceeds the amount by weight of polysaccharide, instantaneously heating said starch/monohydric alcohol slurry while moving said slurry through a confined zone comprising a continuous tubular reactor which is at least 50 feet in length, and in which the slurry is transferred therethrough by fluid pressure only under high temperature and pressure in the presence of an acid catalyst to continuously produce a mixture of alkyl glycosides.

10. The method of claim 9, in which the temperature in the reactor is in the range of 100°-400° C.

11. The method of claim 9, in which the acid catalyst is selected from the group consisting of hydrochloric acid, sulfuric acid, phosphoric acid, ortho-, meta-, and para-toluenesulfonic acid, benzene-sulfonic acid, substituted benzene-sulfonic acid, ethane-sulfonic acid, and combinations of the above, and in which the alcohol is selected from the group consisting of methanol, ethanol, propanol, allyl alcohol, butanol, and alcohols having five to eighteen carbon atoms, their isomers, derivatives and mixtures thereof.

12. The method of claim 11, in which the starch monohydric alcohol slurry is about 40-45% solids, the catalyst comprises at least 0.005 moles of para-toluenesulfonic acid per mole anhydroglucose unit, and the reaction temperature in the confined zone is at least 165° C.

13. The method of claim 11 in which the monohydric alcohol is methanol and the methanol/starch mole ratio in the slurry is in the range of 15:1 to 6.5:1, the reaction temperature in the confined zone is about 160°-180° C., the retention time in the confined zone is about 8-20 minutes, and the catalyst is present in an amount of at least about 0.004 moles per anhydroglucose units.

14. The method of claim 13 wherein the alcoholysis of the slurry within said confined zone is maintained under conditions sufficient to yield a mixture of alkyl glycosides containing from about 65% to 90% alpha- and beta-methyl glucoside.

15. The method of claim 11, in which the retention time of the starch in the confined zone is 5 to 20 minutes, the alcohol is methanol, and the molar ratio of methanol to starch is 6.5:1 to 9:1.

* * * * *

UNITED STATES PATENT AND TRADEMARK OFFICE
CERTIFICATE OF CORRECTION

PATENT NO. : 4,223,129

DATED : September 16, 1980

INVENTOR(S) : Claris D. Roth et al.

It is certified that error appears in the above-identified patent and that said Letters Patent are hereby corrected as shown below:

Column 1, line 49, for "catayst" read ----catalyst----

Column 5, Table I, for "Higher glycosides" read ----Higher methyl-alpha and beta oligosides----

Column 5, Table I, for "alpha-and beta-glucofuranosides----" read ----methyl-alpha-D-glucofuranoside and methyl-beta-D-glucofuranoside----

Column 5, line 59, for "tht" read ----that----

Column 6, Table II, for "methyl-beta" read ----methyl-alpha-D-glucopyranoside----

Column 6, Table II, for "alpha-and beta-methyl diglycosides" read ----methyl-alpha-D-maltoside and methyl-beta-D-maltoside----

Column 6, Table II, for "alpha-and beta-methyl triglycosides" read ----methyl-alpha-D-maltotrioside and methyl-beta-D-maltotrioside----

Column 6, Table II, for "Higher glycosides" read ----Higher methyl-alpha and beta oligosides----

Column 6, Table II, for "alpha-and beta-glucofurnaosides" read ----methyl-alpha-D-glucofuranoside and methyl-beta-D-glucofuranoside----

Column 7, Table III, for "alpha-methyl glucoside" read ----methyl-alpha-D-glucopyranoside----

Column 7, Table III, for "alpha-and beta-methyl diglycosides" read ----methyl-alpha-D-maltoside and methyl-beta-D-maltoside----

Column 7, Table III, for "alpha-and beta-methyl triglycosides" read ----methyl-alpha-D-maltotrioside and methyl-beta-D-maltotrioside----

Column 7, Table III, for "Higher glycosides" read ----Higher methyl-alpha and beta oligosides----

Column 7, Table III, for "alpha- and beta-glucofuranosides" read ----methyl-alpha-D-glucofuranoside and methyl-beta-D-glucofuranoside----

UNITED STATES PATENT AND TRADEMARK OFFICE
CERTIFICATE OF CORRECTION

PATENT NO. : 4,223,129
DATED : September 16, 1980
INVENTOR(S) : Claris D. Roth et al.

It is certified that error appears in the above-identified patent and that said Letters Patent are hereby corrected as shown below:

Column 7, Table IV, for "apha-methyl glucoside" read ---methyl-alpha-D-glucopyranoside---
Column 7, Table IV, for "alpha-and beta-methyl diglycosides" read ---methyl-alpha-D-maltoside and methyl-beta-D-maltoside---
Column 7, Table IV, for "alpha-and beta-methyl triglycosides" read ---methyl-alpha-D-maltotrioside and methyl-beta-D-maltotrioside---
Column 7, Table IV, for "Higher glycosides" read ---Higher methyl-alpha and beta oligosides---
Column 7, Table IV, for "alpha-and beta-glucofuranosides" read ---methyl-alpha-D-glucofuranoside and methyl-beta-D-glucofuranoside---
Column 7, line 61, for "alpha-methyl glucosides" read ---methyl-alpha-D-glucopyranoside---
Column 8, Table V, for "alpha-methyl glucoside" read ---methyl-alpha-D-glucopyranoside---
Column 8, Table V, for "alpha-and beta-methyl diglycosides" read ---methyl-alpha-D-maltoside and methyl-beta-D-maltoside---
Column 8, Table V, for "alpha-and beta-methyl triglycosides" read ---methyl-alpha-D-maltotrioside and methyl-beta-D-maltotrioside---
Column 8, Table V, for "Higher glucosides" read ---Higher methyl-alpha and beta oligosides---
Column 8, Table V, for "alpha-and beta-glucofuranosides" read ---methyl-alpha-D-glucofuranoside and methyl-beta-D-glucofuranoside---

UNITED STATES PATENT AND TRADEMARK OFFICE
CERTIFICATE OF CORRECTION

PATENT NO. : 4,223,129

DATED : September 16, 1980

INVENTOR(S) : Claris D. Roth et al.

It is certified that error appears in the above-identified patent and that said Letters Patent are hereby corrected as shown below:

Column 8, Table VI, for "alpha-methyl glucoside" read ---metyyl-alpha-D-glucopyranoside---
Column 8, Table VI, for "alpha-and beta-methyl diglycosides" read ---methyl-alpha-D-maltoside and methyl-beta-D-maltoside---
Column 8, Table VI, for "alpha-and beta methyl triglycosides" read ---methyl-alpha-D-maltotrioside and methyl-beta-D-maltotrioside---
Column 8, Table VI, for "Higher glycosides" read ---Higher methyl-alpha and beta-oligosides---
Column 8, Table VI, for "alpha-and beta-glucofuranosides" read ---methyl-alpha-D-glucofuranoside and methyl-beta-D-glucofuranoside---
Column 8, line 64, for "alpha-methyl glucoside" read ---methyl-alpha-D-glucopyranoside---

Signed and Sealed this

Fourteenth Day of July 1981

[SEAL]

Attest:

Attesting Officer

GERALD J. MOSSINGHOFF

Commissioner of Patents and Trademarks